United States Patent [19]
Lajus et al.

[11] Patent Number: 4,922,512
[45] Date of Patent: May 1, 1990

[54] ISOCENTRIC X-RAY EQUIPMENT STAND HAVING FOUR AXES OF ROTATION

[75] Inventors: Pierre Lajus, Meudon; Jean Caugant, Chevilly Larue, both of France

[73] Assignee: General Electric CGR SA, Paris, France

[21] Appl. No.: 360,608

[22] Filed: Jun. 2, 1989

[30] Foreign Application Priority Data

Jun. 3, 1988 [FR] France .................. 88 07442

[51] Int. Cl.⁵ .................................. H05G 1/02
[52] U.S. Cl. ........................... 378/197; 378/195
[58] Field of Search ............. 378/195, 196, 197, 198

[56] References Cited

U.S. PATENT DOCUMENTS 2,818,510 12/1957 Verse .................... 378/189
4,741,015 4/1989 Charrier ................ 378/197

Primary Examiner—Craig E. Church
Attorney, Agent, or Firm—Oblon, Spivak, McClelland, Maier & Neustadt

[57] ABSTRACT

In an x-ray equipment stand designed to perform isocentric scanning movements and having three axes of rotation concurrent to the isocenter O, the isocenter can be caused to rotate about a fourth axis (Axis 4) perpendicular to the second axis (Axis 2) and parallel to the third axis (Axis 3). This permits displacement of the isocenter in the horizontal plane, especially along straight lines which are secant with the third axis.

6 Claims, 4 Drawing Sheets

ISOCENTRIC X-RAY EQUIPMENT STAND HAVING FOUR AXES OF ROTATION

BACKGROUND OF THE INVENTION

1. Field of the Invention

The invention relates to x-ray installations and, more particularly in an installation of this type, to an x-ray equipment stand which permits isocentric scanning or examination of a patient at multiple angles of incidence.

2. Description of the Prior Art

X-ray examination of a patient is performed by means of an imaging chain which, as a general rule, is essentially constituted by an x-ray source, a collimator, an anti-diffusion grid and a receiver which are carried in rigidly assembled relation by a structure known as a stand.

The x-ray source and the collimator are located on the same side with respect to the patient to be examined who is placed on a table whilst the anti-diffusion grid and the receiver are on the opposite side. A straight line passing through the focus of the x-ray source and the center of the receiver represents the axis of x-radiation or imaging chain axis. In the case of isocentric scanning or examination, this axis always passes through the same point of a zone to be scanned irrespective of the orientation of said axis and this point constitutes the isocenter. The movement which makes it possible to vary the orientation of the imaging chain axis with respect to the isocenter is known as an isocentric movement.

Stands which serve to carry out an isocentric movement usually consist of an open arch or arcuate member, one end of which carries the x-ray source and the other end of which carries the receiver. The axis of the imaging chain passes through the isocenter which constitutes the center of the arcuate member or is located on the same axis as the center of the arcuate member so that a first isocentric movement is performed by rotating the arcuate member about its center in its plane, for example by displacing the arcuate member in sliding motion within a sleeve having the shape of a circular arc.

X-ray equipment stands permit in addition a second isocentric movement which consists of rotation of the plane of the arcuate member about a second axis of rotation which is perpendicular to the first and also passes through the isocenter.

In certain x-ray equipment stands, provision is made for a third isocentric movement which consists of a rotation about a third axis of rotation which is perpendicular to the plane of the first and second axes and passes through the isocenter.

It is apparent that these three isocentric movements make it possible to take pictures of the patient in incidence and in planes which can be oriented in all directions in space.

In an x-ray installation, the patient is placed on a table which permits displacements of the patient in three directions, namely one direction in elevation (z-axis) and two directions in the horizontal plane (x-axis in the longitudinal direction of the patient and y-axis in the perpendicular direction). The aim of these movements is to cause the isocenter to coincide with the center of the zone to be examined.

An installation of this type is attended by a certain number of disadvantages. One disadvantage lies in the fact that it is cumbersome since it calls for the use of a patient support table which moves in the horizontal plane so as to place the center of the zone to be observed at the isocenter of the stand.

Another disadvantage is that the stand has considerable overhang since it has to permit longitudinal displacement of the patient over a substantial width. This also has the effect of increasing the bulk of the installation.

SUMMARY OF THE INVENTION

One object of the present invention is therefore to construct an isocentric x-ray equipment stand which makes it possible to take pictures of the patient in incidence without any need to displace the patient in order to cause the isocenter to coincide with the center of the zone to be examined.

Another object of the present invention is to construct an isocentric x-ray equipment stand which makes it possible to reduce the bulk of the x-ray installation.

The invention relates to an isocentric x-ray equipment stand which comprises an X-ray source and an x-ray detector carried by an arcuate member and defining an imaging chain axis which passes through an isocenter, said arcuate member being capable of displacement in rotational motion about a first axis (Axis 1) perpendicular to the plane of the arcuate member and passing through the isocenter as well as about a second axis (Axis 2) in the plane of the arcuate member perpendicular to the first axis and also passing through the isocenter, said arcuate member being supported by a rigid structure which pivots about a third axis (Axis 3) perpendicular to the first and second axes and passing through the isocenter.

The invention is distinguished by the fact that it includes rotation means for causing the isocenter to rotate about a fourth axis (Axis 4) perpendicular to the second axis and parallel to the third axis.

DETAILED DESCRIPTION OF THE INVENTION

Figure 1:
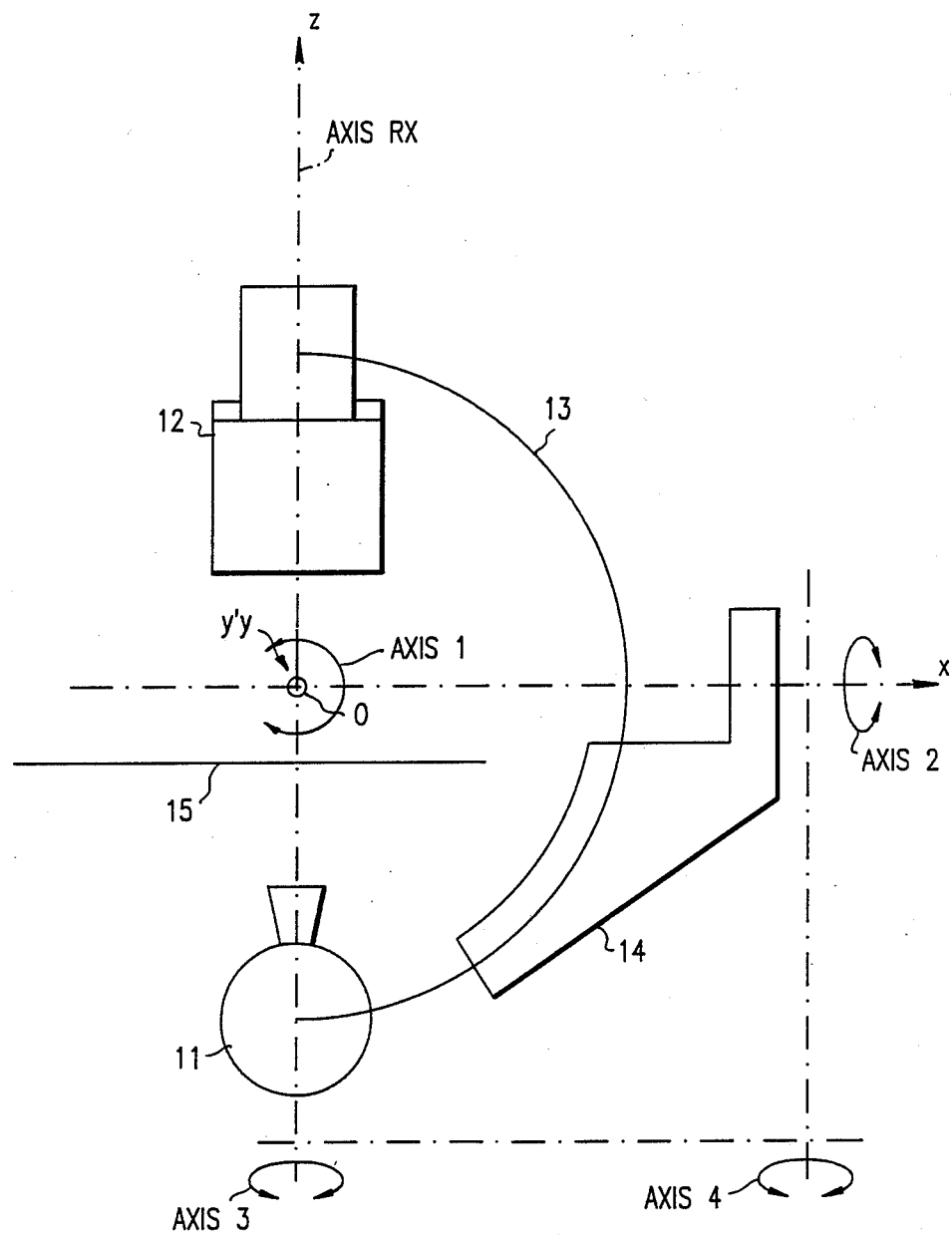
FIG. 1 is a view which shows diagrammatically the relative positions of the different axes of rotation of an equipment stand in accordance with the invention.

In FIG. 1, which is a view showing diagrammatically the relative positions of the different axes of rotation of an equipment stand in accordance with the invention, there are shown the three orthogonal axes x'x and y'y in the horizontal plane and z'z in the vertical plane which are concurrent to a point 0. The stand comprises an arcuate member 13 which supports an x-ray source 11 and a detector 12 placed along the diameter of the arcuate member. Said arcuate member is supported by a sleeve or guide 14 within which it is capable of sliding under the control of the operator. A patient support table 15 or so-called examination table is placed between the x-ray source 11 and the detector 12 in the longitudinal direction x'x and slightly beneath the horizontal plane defined by the axes x'x and y'y.

A displacement of the arcuate member 13 in sliding motion makes it possible to carry out a rotation of the x-ray source and of the detector about an axis 1 perpendicular to the plane which contains these two elements, which means that the axis of the x-ray beam describes a surface in a plane parallel to said plane. In the particular case of FIG. 1, the Axis 1 coincides with the axis y'y.

The sleeve 14 is capable of rotating about an Axis 2 located in a horizontal plane which passes through the point 0 known as the isocenter. In this particular case of FIG. 1, said Axis 2 coincides with the axis x'x. As a result of rotation of the arcuate member 13 about the Axis 2, the axis of the x-ray beam can be caused to describe a surface perpendicular to the plane of the arcuate member.

The support of the Axis 2 (not shown in the drawings) is capable of rotating about an Axis 3 which coincides with the vertical axis z'z and therefore passes through the isocenter 0. This rotation about the Axis 3 makes it possible to displace the arcuate member 13 on each side of the examination table or in other words to provide freedom of access to the patient's head.

These three rotations about the Axes 1, 2 and 3 serve to scan zones of the patient's body at angles of incidence which have any directions in space but which all pass through the isocenter 0. It is accordingly apparent that, in order to examine another organ of the patient's body, this latter or in other words the examination table has to be displaced with a view to bringing the center of this other organ to the isocenter 0.

In accordance with the invention, it is proposed to displace the isocenter 0 so that this latter can be made to coincide with the center of the zone of the patient to be observed by providing for rotation of the Axis 2 about an Axis 4 which is perpendicular to the Axis 2 and located in the plane containing the Axis 3 in the case of the particular position of FIG. 1. This rotation about the Axis 4 makes it possible to displace the isocenter 0 in the horizontal plane defined by the axes x'x and y'y by causing it to describe a circular arc. Since the Axis 4 is in any case capable of rotating about the Axis 3, it is possible to cause the isocenter 0 to describe any curve in the horizontal plane by combining the two angular movements about the Axes 3 and 4.

Figure 2:
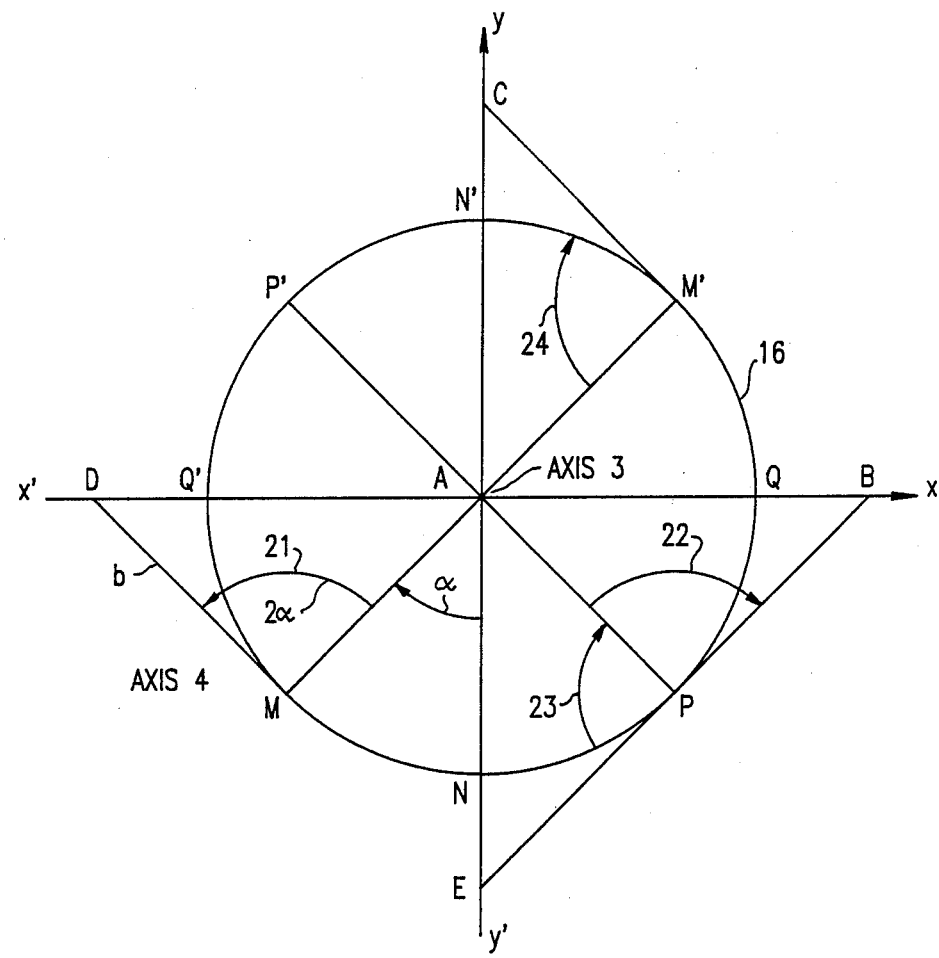
FIG. 2 is a geometrical drawing showing the rectilinear displacement which can be obtained by means of two coordinated angular movements.

The geometrical diagram of FIG. 2 serves to gain an understanding of the movements which can be performed by virtue of the presence of said Axis 4. This diagram has been drawn in the horizontal plane and the point A materializes the position of the isocenter as well as that of the axis z'z or Axis 3. The Axis 4 is therefore capable of moving on a circle 16 having a center A so as to cover approximately an angle of 135° on each side of the axis x'x as it passes on the side corresponding to the patient's head. The fact that the angle is limited to approximately 135° on each side is due to the presence of the examination table support on the side corresponding to the patient's feet. In respect of each position on said circle 16, the equipment stand has three concurrent axes, thus permitting all angles of incidence about the isocenter.

It may also be understood from FIG. 2, that, by virtue of the combination of the angular movement about the Axis 3 and of the angular movement of the Axis 2 about the Axis 4, the isocenter can be made to describe the segment DB on the axis x'x and the segment EC on the axis y'y. The law which associates the two angular movements must be such that, when the Axis 4 rotates through an angle $\alpha$ about the Axis 3, the Axis 2 must rotate through an angle $2\alpha$ about the Axis 4.

Thus, when the Axis 4 is in position N, that is to say on the axis y'y, the isocenter is at the point A. If the Axis 4 rotates through the angle $\alpha$ in order to move to position M, the isocenter will be on x'x at the point D if the Axis 2 rotates through an angle $2\alpha$ about the Axis 4 in the direction 4 defined by the arrow 21. In fact, the triangle defined by the points A, M and D must always be isosceles with the side b equal to the distance between axes of the equipment stand or in other words the distance between the isocenter and the Axis 4. As a result, the vertex angle must be equal to $2\alpha$ if the angle MAN is equal to $\alpha$.

When the Axis 4 passes from N to P, the isocenter will describe the segment AB if the Axis 2 rotates in the direction defined by the arrow 22. It is understood that the isocenter can describe the segments AB and AD when the Axis 4 describes respectively the circular arcs N'M' and N'P'.

In order to ensure that the isocenter describes the segment EA, the Axis 4 must describe the circular arc PQ whilst the Axis 2 must rotate in the direction indicated by the arrow 23. In the case of AC, the Axis 4 must describe the circular arc QM' whilst the Axis 2 must rotate in the direction of the arrow 24. It will be understood that, in this case also, the isocenter can describe the segments AE and AC when the Axis 4 describes the circular arcs Q'M and Q'P' but this possibility is not put to use since the support of the examination table prevents displacement over part of the circular arc P'Q'M.

The length of the segments described by the isocenter on the axes x'x and y'y is given by the formula $$2b \sin \alpha$$

as determined by means of the trigonometric relations of the isosceles triangle DMA, for example.

The principles demonstrated in the foregoing in regard to displacement of the isocenter on the axes x'x and y'y can be demonstrated in the case of any other system of orthogonal axes which is inclined with respect to the axes x'x/y'y. This shows that the isocenter can be displaced to any point of the horizontal plane defined by x'x and y'y but within a circle having a radius $2b \sin \alpha$ and having a center A.

It is worthy of note that the radius of this circle is limited by the maximum value which can be assumed by the angle $\alpha$, taking into account the presence of the examination table.

When the isocenter describes the segments AD, AB, AE and AC, the x-ray beam follows the angular movement about the Axis 3 and rotates through an angle $\alpha$. As a result, the image received by the detector also rotates and corrections therefore have to be made in order to ensure that it retains the same orientation in space. These corrections can be obtained by making use of electronic means and/or methods for producing action on the image itself or by making use of means for producing action directly on the orientation of the detector as a function of the value of the angle $\alpha$.

Figure 3:
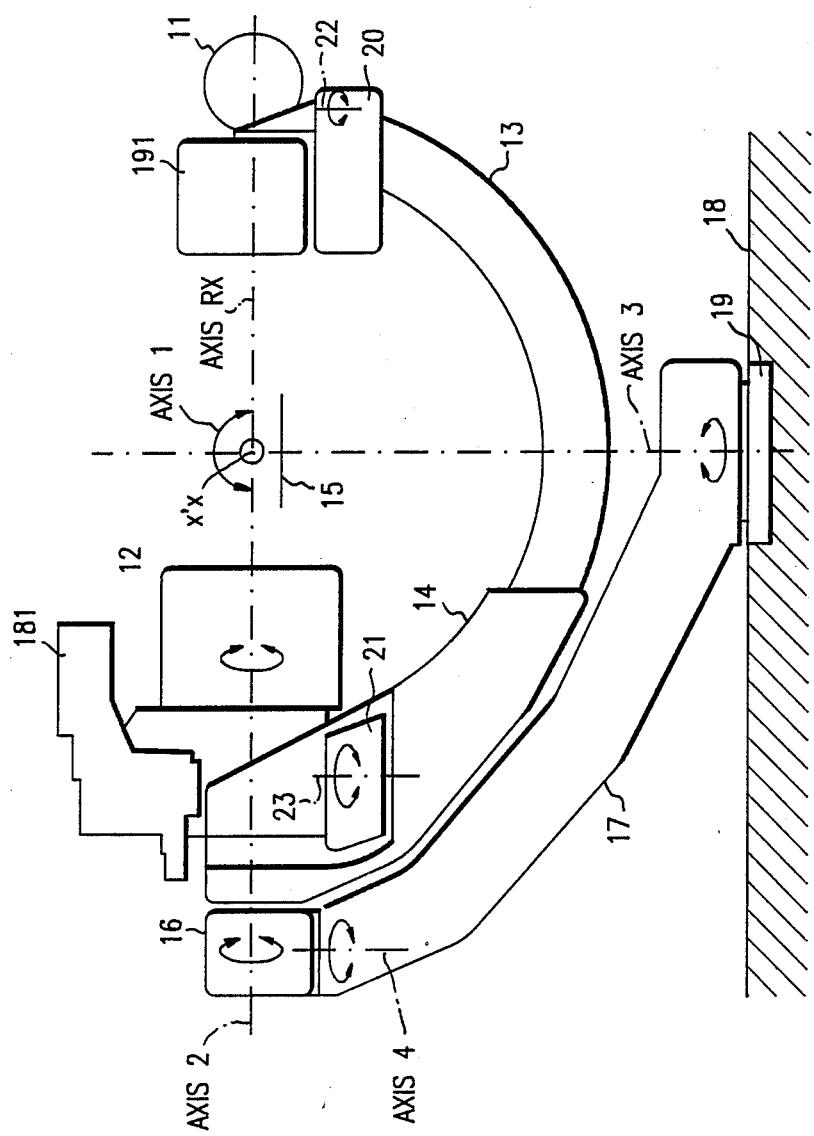
FIG. 3 is a view in elevation showing one example of construction of an equipment stand in accordance with the invention.

FIG. 3 is a view in elevation of one example of construction of an equipment stand for carrying out the invention described with reference to FIGS. 1 and 2. In FIG. 3, the elements which are identical with those of FIG. 1 are designated by the same references. The sleeve 14 is carried by an element 16 and this latter carries the rotating shaft which materializes the Axis 2. Said shaft is capable of rotating through an angle of plus or minus 180°, which means that the arcuate member is capable of performing one complete revolution about the Axis 2. The element 16 is carried at the upper end of a rigid structure 17 having the shape of a circular arc, the lower end of which is capable of pivoting about the Axis 3 between −135° and +135°. This Axis 3 is materialized by a shaft which is fixed on the ground 18 by means of a base 19. In accordance with the invention, the element 16 is mounted for pivotal displacement about the Axis 4 which is vertically mounted at the upper end of the pivoting structure 17. The angular movement is limited between the positions −90° and +90°.

The detector 12 is pivotally mounted so as to rotate about the axis of the x-ray beam. This makes it possible to maintain the same orientation for the image irrespective of the angular movements about the Axes 3 and 4.

The equipment stand which has just been described can be associated with elements which are employed in equipment stands of the prior art. It is thus possible to associate a collimation 191 with the x-ray source and an imaging chain 181 with the x-ray detector 12. It is also possible to mount the x-ray source and the detector on sliding devices 20 and 21 respectively so as to carry out their relative displacement on the axis RX.

It is also possible to mount the x-ray source and the detector on axes 22 and 23 respectively in order to operate with incident rays on the detector or on an ancillary detector. It is also possible to displace the Axis 2 vertically so as to obtain a variable position of the isocenter in height.

Figure 4:
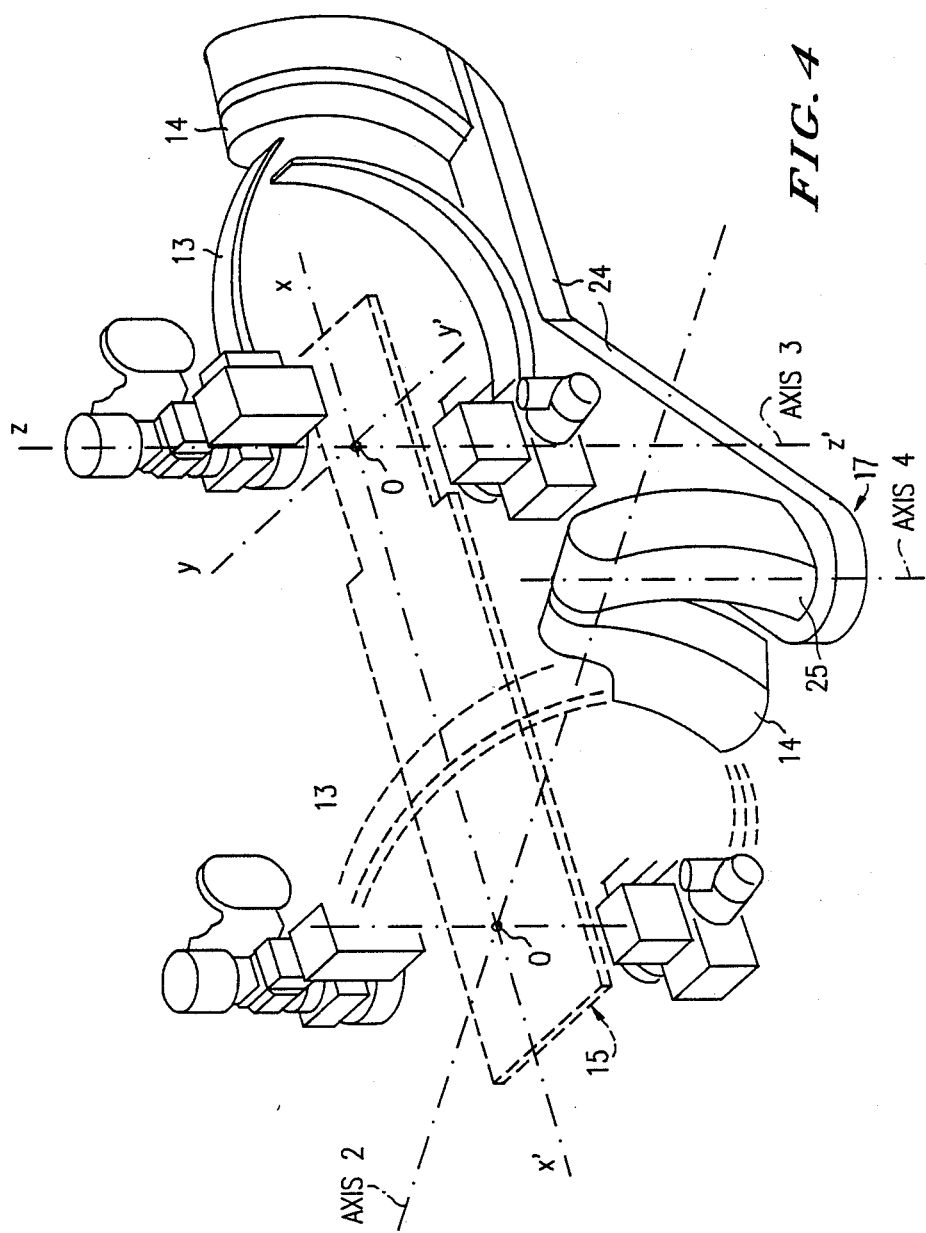
FIG. 4 is a view in isometric perspective showing an x-ray installation which makes use of an isocentric equipment stand in accordance with the invention.

FIG. 4 is a diagram in isometric perspective showing another example of construction of an equipment stand in accordance with the invention in which the pivot of the Axis 4 is located at ground level and not in elevation as is the case with the equipment stand of FIG. 3. Provision is accordingly made for an arm 17 which rests and moves on the ground, thus avoiding the need to have a cantilevered arm 17. In this figure, elements which are identical with those of the previous figures are designated by the same references.

FIG. 4 shows two positions of the equipment stand, namely one position in which the isocenter 0 is located at the center on the patient's head and the other position in which the isocenter 0 has been brought to the level of the patient's lower limbs. This figure has the main advantage of showing that the equipment stand in accordance with the invention makes it possible to obtain a scan of the isocenter 0 over a patient's entire body without having to displace the examination table. It also shows that this equipment stand permits freedom of access to the patient's head or to one of the longitudinal sides according to the operator's requirements. This results in reduced bulk of the x-ray installation while providing greater flexiblity of use of the equipment stand.

More precisely, the equipment stand of FIG. 4 differs from that of FIG. 3 in regard to the manner in which the rigid structure 17 is constructed. The arcuate structure 17 has been replaced by an equivalent structure having a horizontal portion 24 which rests on the ground and moves in rotation on this latter by pivoting about the Axis 3. That end of said horizontal portion 24 which is opposite to the end of the Axis 3 supports a vertical portion 25 mounted for pivotal motion about the Axis 4 which is in rigidly fixed relation to the horizontal portion 24. This vertical portion 25 in turn supports the arcuate member 13 and its associated rotation means.

The invention has been described in connection with particular examples of construction but may clearly be carried out in different ways without thereby departing from its scope as defined by the appended claims:

What is claimed is:

1. An isocentric x-ray equipment stand, comprising:
   an X-ray source;
   an X-ray detector;
   an arcuate member carrying said source and said detector wherein said arcuate member defines an imaging chain axis which passes through an isocenter, said arcuate member being displaceably mounted for rotation about a first axis perpendicular to the plane of said arcuate member and passing through the isocenter wherein said arcuate member is also displaceably positioned for rotation about a second axis in the plane of the arcuate member or in a parallel plane perpendicular to said first axis and also passing through said isocenter;
   a rigid structure supporting said arcuate member wherein said rigid structure is pivotably mounted about a third axis perpendicular to said first and second axis and passing through said isocenter; and
   rotation means for causing said isocenter to rotate about a fourth axis perpendicular to said second axis and parallel to said third axis.

2. An isocentric x-ray equipment stand according to claim 1, wherein the rigid structure has the shape of a circular arc, one end of which is pivotally fixed on the ground and the other end of which is adapted to support the arcuate member and its associated means for rotation about the first and second axes as well as the means for rotation of the isocenter about the fourth axis.

3. An X-ray equipment stand according to claim 2, wherein the rigid structure has a first horizontal portion which rests and moves on the ground while pivoting about the Axis 3 and a second vertical portion which supports the arcuate member and its associated means for rotation about the first and second axes as well as supporting the means for rotation of the isocenter 0 about the fourth axis (Axis 4).

4. An x-ray equipment stand according to claim 1, wherein means are provided for allowing coordinated angular displacements about the third axis (Axis 3) and fourth axis (Axis 4) so as to displace the isocenter along a predetermined path in the horizontal plane which passes through the isocenter.

5. An x-ray equipment stand according to claim 4, wherein said path of displacement of the isocenter is a straight line which is secant with the third axis and is obtained by an angular displacement about the fourth axis which angular displacement is double the angular displacement about the third axis.

6. An x-ray equipment stand according to claim 1, wherein the x-ray detector is pivotally mounted for rotating about the axis RX of the imaging chain so as to compensate for rotation of the image at the time of angular movements about the third and fourth axes.

* * * * *